(12) United States Patent
Keller

(10) Patent No.: US 6,981,990 B2
(45) Date of Patent: Jan. 3, 2006

(54) CERVICAL PROSTHESIS WITH INSERTION INSTRUMENT

(75) Inventor: Arnold Keller, Kayhude (DE)

(73) Assignee: Cervitech, Inc., Rockaway, NJ (US)

( * ) Notice: Subject to any disclaimer, the term of this patent is extended or adjusted under 35 U.S.C. 154(b) by 0 days.

(21) Appl. No.: 10/633,309

(22) Filed: Aug. 4, 2003

(65) Prior Publication Data

US 2005/0033428 A1 Feb. 10, 2005

(51) Int. Cl.
*A61F 2/44* (2006.01)

(52) U.S. Cl. .................................... 623/17.11

(58) Field of Classification Search ............ 623/17.11, 623/17.12, 17.13, 17.14, 17.15, 17.16; 606/211, 606/53, 86, 99; 206/63.5, 438; 433/172, 433/173
See application file for complete search history.

(56) References Cited

U.S. PATENT DOCUMENTS

| | | | | |
|---|---|---|---|---|
| 3,916,907 | A | * | 11/1975 | Peterson ..................... 606/90 |
| 5,122,130 | A | * | 6/1992 | Keller ......................... 606/61 |
| 5,984,922 | A | * | 11/1999 | McKay ........................ 606/61 |
| 6,113,639 | A | * | 9/2000 | Ray et al. ................. 623/17.16 |
| 6,159,215 | A | * | 12/2000 | Urbahns et al. ............... 606/86 |
| 6,168,631 | B1 | * | 1/2001 | Maxwell et al. .......... 623/21.18 |
| 6,395,031 | B1 | * | 5/2002 | Foley et al. ............. 623/17.11 |
| 6,416,324 | B1 | * | 7/2002 | Day ........................... 433/173 |
| 6,752,832 | B2 | * | 6/2004 | Neumann ................ 623/17.15 |
| 2002/0082695 | A1 | * | 6/2002 | Neumann ................ 623/17.11 |
| 2003/0083747 | A1 | * | 5/2003 | Winterbottom et al. .. 623/17.11 |

FOREIGN PATENT DOCUMENTS

| | | |
|---|---|---|
| FR | 2795945 A1 | 1/2001 |
| WO | WO-01/06962 A1 | 2/2001 |
| WO | WO-03/026522 A2 | 4/2003 |
| WO | WO-03/037228 A2 | 5/2003 |

OTHER PUBLICATIONS

European Search Report dated Jan. 8, 2004.

* cited by examiner

*Primary Examiner*—Kevin Shaver
*Assistant Examiner*—Annette Reimers
(74) *Attorney, Agent, or Firm*—Morrison & Foerster LLP

(57) ABSTRACT

A device for implanting a cervical prosthesis includes a cervical prosthesis, an insertion instrument, and a holder which facilitates the connection of the gripping members of the insertion instrument to the prosthesis. The holder receives the prosthesis with an exact fit and has, on the anterior face of the prosthesis, an opening for admission of the gripping members of the insertion instrument. The opening contains guide elements for guiding the gripping members of the insertion instrument into a removal position in which the complementary projections and recesses of the gripping members and of the prosthesis lie opposite one another.

2 Claims, 3 Drawing Sheets

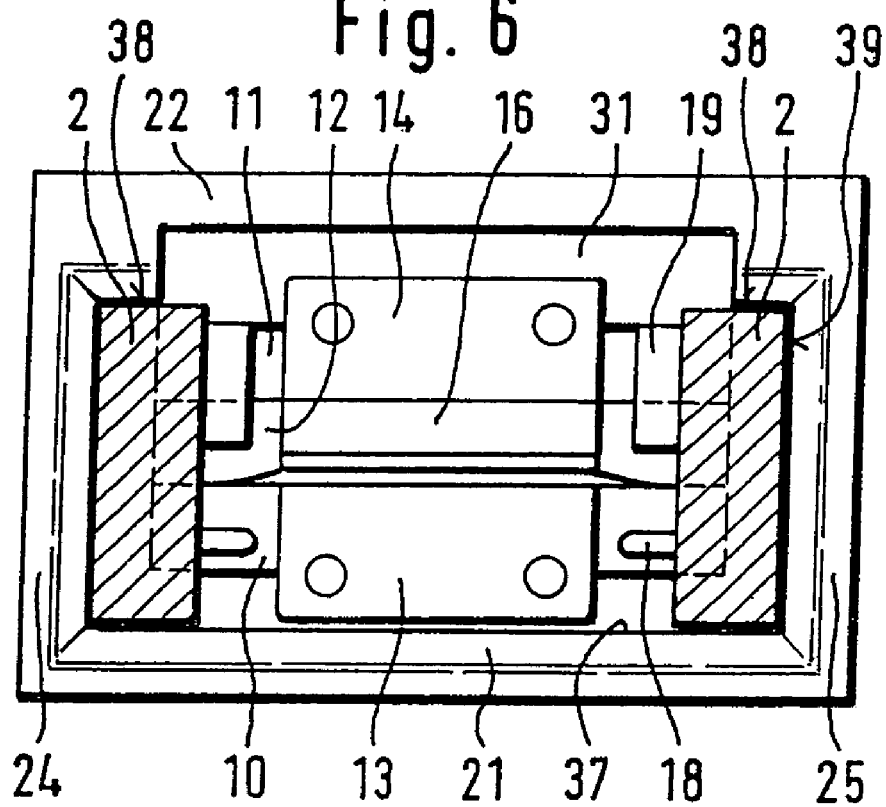

CERVICAL PROSTHESIS WITH INSERTION INSTRUMENT

FIELD AND BACKGROUND OF THE INVENTION

It is known (EP-A 333990) to implant intervertebral prostheses using an insertion instrument with a pair of gripping members which grip the prosthesis on opposite sides. The gripping members connected rigidly to one another each have a groove extending in the A-P direction and receiving the two plate edges which extend in the A-P direction and which are held in said groove by friction or by a spring-mounted catch. When the prosthesis has reached the site in which it is to be implanted, the instrument is removed from it. The plate edges slide in the A-P direction out of the grooves. Gripping members of this kind are suitable only for end plates whose side edges extend parallel to one another and are at a predetermined and always constant distance from one another. They are unsuitable for small prostheses, such as are used in the area of the cervical spine, and for those prostheses which do not have a side edge designed to cooperate with the gripping members. Finally, they are also unsuitable for prostheses which need to be fitted with great precision and whose position relative to the insertion instrument must not be accidentally altered by the forces arising during implantation.

SUMMARY OF THE INVENTION

The object of the invention is to make implantation of a cervical prosthesis with an insertion instrument more reliable.

The solution according to the invention lies in the structure of the invention as disclosed hereinafter.

The invention makes use of an arrangement consisting of a cervical prosthesis and of an insertion instrument whose gripping members for gripping the prosthesis on opposite sides can be moved toward one another and away from one another. The prosthesis and the gripping members are provided with complementary projections and recesses which, with a form fit, define the position in the A-P direction of the prosthesis. As long as the gripping members are closed about the prosthesis, then, in contrast to the known arrangement described above, the prosthesis cannot change its position relative to the insertion instrument in the plane parallel to the extent of the prosthesis plates. Therefore, they also cannot slip out of the gripping members in the A-P direction. However, it is not entirely a simple matter to mount the prosthesis parts on the insertion instrument, because the projections and recesses are very small. Moreover, it can also easily happen that a mounting which is done incorrectly goes unnoticed.

A holder is also provided which receives the prosthesis with an exact fit. This ensures that the projections and also the recesses on the prosthesis are located at a predetermined position on the holder. On the side corresponding to the anterior face of the prosthesis, the holder is open to permit removal of the prosthesis. It has guide elements by means of which the gripping members of the insertion instrument are guided into a position, relative to the prosthesis, in which the complementary projections and recesses on the prosthesis and on the gripping members lie level with and opposite one another ready to engage. When the operating surgeon, starting from this position, closes the gripping members, the projections and recesses safely engage and the desired, correct mounting of the prosthesis on the insertion instrument is reliably obtained.

To ensure that the prosthesis adopts and maintains the exact fit position in the holder, releasable means for fixing the prosthesis in this position are expediently provided on the holder. The release function of these means can be based on their being able to yield elastically when the prosthesis mounted on the insertion instrument is withdrawn from the holder. The release function can also involve the means, or their attachment to the holder, being destroyed upon removal of the prosthesis. The means can also be a lid which secures the prosthesis in the holder and is opened for removal of the prosthesis. Finally, it is also possible for the holder as a whole to be destroyed, for example by its being provided with predetermined break points or tear lines. The holder can be a disposable article.

BRIEF DESCRIPTION OF THE DRAWINGS

The invention is explained in more detail below with reference to the drawings which show diagrams of an advantageous illustrative embodiment, and in which:

FIG. 6 shows a ventral view of the holder with the prosthesis located in it and gripping members appearing in section.

DETAILED DESCRIPTION OF THE INVENTION

Figure 1:
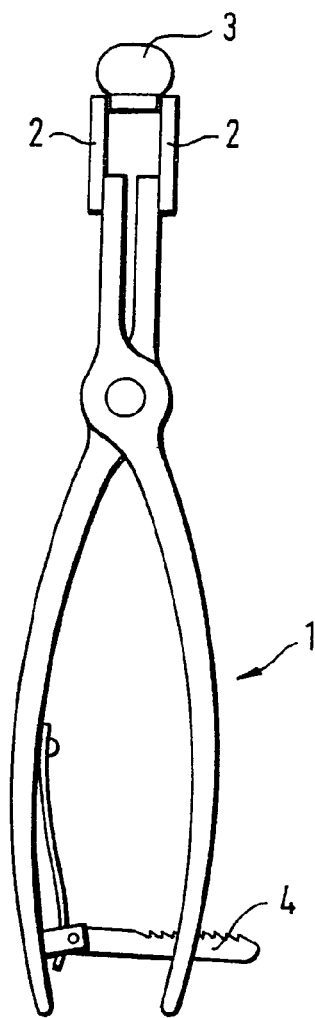
FIG. 1 shows an overall view of an insertion instrument with cervical prosthesis.
Figure 2:
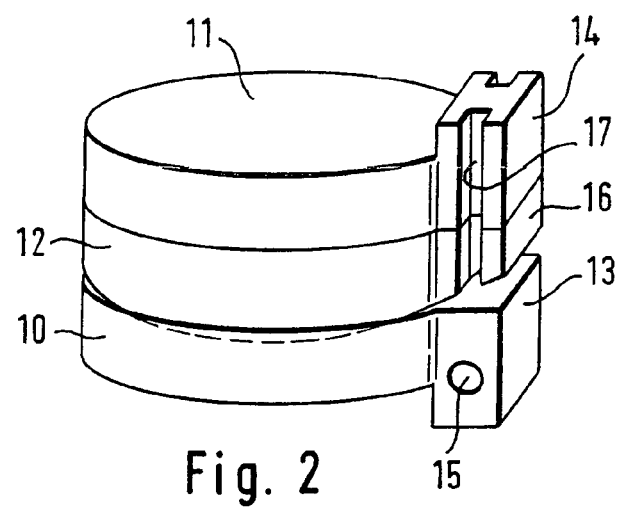
FIG. 2 shows the prosthesis in a perspective view and at a larger scale.
Figure 3:
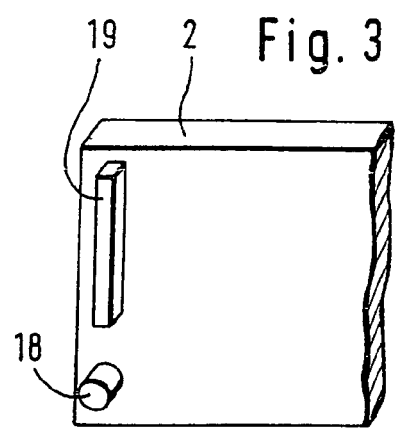
FIG. 3 shows the gripping member of the insertion instrument.

The insertion instrument 1 is designed as a forceps which, at the front end, has a pair of gripping members 2 which grip the prosthesis 3 from opposite sides. In the example shown, the A-P (anterior-posterior) direction coincides with the longitudinal direction of the insertion instrument. This is preferable. However, the longitudinal direction of the instrument can also deviate slightly from the A-P direction of the prosthesis. In FIG. 2 the dorsal face of the prosthesis is arranged on the left. The forceps can be secured in the closed position by a releasable lock 4.

According to FIG. 2, the prosthesis consists of two cover plates 10, 11 and of a prosthesis core 12 which forms a hinge with the cover plate 10. The height of the prosthesis can be varied, namely by using prosthesis cores 12 of different heights. Along their ventral edge, the cover plates 10, 11 each have a flange 13, 14 which is slightly narrower than the plate-shaped parts of the cover plates 10, 11 and of the prosthesis core 12. In each of its side faces, the flange 13 of the cover plate 10 has a bore 15. The flange 14 of the cover plate 11 and the corresponding part 16 of the prosthesis core 12 have, in their side faces, a slit 17 extending perpendicularly with respect to the extent of the plates. Both sides are of identical and symmetrical design.

The gripping members 2 have a pin 18 corresponding to each bore 15, and a protruding ridge 19 corresponding to each slit 17. The reason for choosing a slit 17 on the parts 11, 12 lies in the fact that the prosthesis core 12 can have different heights. The ridge 19 can cooperate with slits 17 of parts 11, 12 of different height.

The holder 20 consists of a lower wall 21, an upper wall 22, a rear wall 23, and side walls 24, 25. It is open at the front 26. The walls delimit a space 27 for receiving the prosthesis 3. Its height can correspond exactly to the height of a prosthesis. So that the same holder type can be used for prostheses of different heights, it is preferable if its overall height between the inner faces 30 of the lower wall 21 and of the upper wall 22 is slightly greater than the height of the prostheses and if the remaining space is closed by a filler piece 31 which has a thickness adapted to the respective prosthesis height. The height position of the prosthesis in the holder is in any event precisely fixed.

In the L-M (lateral-medial) direction, the position of the prosthesis in the holder is defined by the side walls 24, 25.

The lower wall 21 and the filler piece 31 have end faces 32, 33 which form abutment surfaces for the dorsal faces of the flanges 13, 14 and thus define the position of the prosthesis in the holder 20 in the A-P direction. The prosthesis is secured in this position by resilient tongues 35 on the side walls 24, 25, which tongues serve as flexible fixing means for the prosthesis in the holder. Their force is such that the prosthesis remains securely in the precise position relative to the holder under the forces which arise during transport, storage and handling. The operating surgeon can thus be assured that the prosthesis is in this position inside the holder when he wishes to connect it to the insertion instrument 1.

Figure 4:
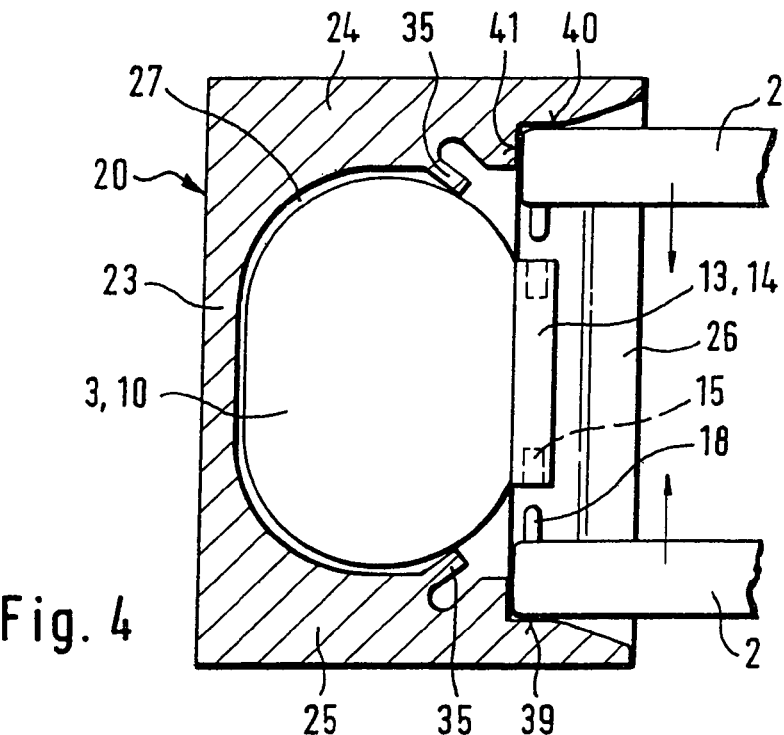
FIG. 4 shows the holder, with the prosthesis located in it, in cross section parallel to the prosthesis plane.
Figure 5:
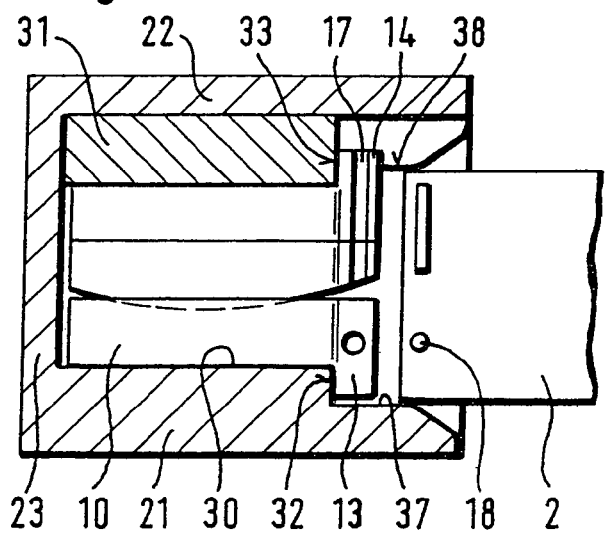
FIG. 5 shows a cross section through the holder along the sagittal plane of the prosthesis located in it.

The opening 26 of the holder 20 is bordered by lower and upper guide surfaces 37, 38 and lateral guide surfaces 39, 40. These surfaces terminate at end faces 41 which can coincide with the abutment surfaces 32, 33. The distance between the upper and lower surfaces 37, 38 of the opening is equal, with slight play, to the height of the gripping members 2 of the insertion instrument. The width between the lateral surfaces 39, 40 of the opening is equal to the width of the instrument in a sufficiently widely opened state. The surfaces 37 to 41 are therefore suitable for positioning the gripping members 2 of the insertion instrument before connection to the prosthesis. The sizes are chosen such that, in this position, the projections 18, 19 of the gripping members and the recesses 15, 17 of the prosthesis lie opposite one another, exactly level and ready to engage. When the gripping members 2 of the insertion instrument are pressed together from this position in the direction of the arrows indicated in FIG. 4, the projections and the recesses come safely into correct engagement with one another. The closed position of the gripping members is secured by the lock 4. The holder can now be removed from the prosthesis 3, held in the insertion instrument, by elastic deformation of the tongues 35.

What is claimed is:

1. A device for implanting cervical prostheses, comprising a cervical prosthesis, an insertion instrument including a pair of gripping members which are configured to grip the cervical prosthesis on opposite sides of the cervical prosthesis, and a holder, separate from the insertion instrument, configured to receive the cervical prosthesis with an exact fit, wherein the gripping members and the prosthesis have complementary projections and recesses which are configured to precisely define the relative position of the prosthesis at least in an anterior-posterior direction and which are configured to be brought into engagement and be released from one another by relative movement of the gripping members in a direction transverse to a longitudinal axis of the insertion instrument and transverse to the anterior-posterior direction of the prosthesis, and wherein the holder comprises an opening with guide elements formed therein for guiding the insertion instrument into a removal position in which the complementary projections and recesses lie opposite one another.

2. The device of claim 1, further comprising a releasable member for fixing the prosthesis in the exact fit position in the holder.

* * * * *